United States Patent [19]
Pollak

[11] Patent Number: 5,804,158
[45] Date of Patent: Sep. 8, 1998

[54] SEQUESTERED IMAGING AGENTS

[75] Inventor: Alfred Pollak, Toronto, Canada

[73] Assignee: Resolution Pharmaceuticals Inc., Mississauga, Canada

[21] Appl. No.: 454,859

[22] Filed: May 31, 1995

[51] Int. Cl.$^6$ .......................... A61K 51/00; A61M 36/14
[52] U.S. Cl. ................ 424/1.69; 424/1.11; 424/1.65; 530/300; 530/328; 530/329; 530/330; 534/14
[58] Field of Search ................... 424/1.69, 1.49, 424/1.65, 9.1, 1.11, 1.37, 1.73, 9.3, 9.4, 9.5; 534/10–16; 530/300, 324–330; 536/1.11, 4.1

[56] References Cited

U.S. PATENT DOCUMENTS

| | | | |
|---|---|---|---|
| 4,421,735 | 12/1983 | Haber et al. | 424/1.11 |
| 4,678,667 | 7/1987 | Meavrs et al. | 424/85 |
| 4,946,668 | 8/1990 | Daddona et al. | 424/534 |
| 4,980,147 | 12/1990 | Fritzberg et al. | 424/534 |
| 5,171,563 | 12/1992 | Abrams et al. | 424/1.69 |
| 5,242,679 | 9/1993 | Fritzberg et al. | 424/1.69 |
| 5,480,970 | 1/1996 | Pollak et al. | 530/328 |
| 5,556,982 | 9/1996 | Fritzberg et al. | 548/303.7 |
| 5,569,745 | 10/1996 | Goodbody et al. | 530/328 |
| 5,662,885 | 9/1997 | Pollak et al. | 424/1.69 |

FOREIGN PATENT DOCUMENTS

| | | | |
|---|---|---|---|
| WO 95/03280 | 2/1995 | WIPO | C07D 213/77 |
| WO 93/03772 | 3/1995 | WIPO | A61K 49/02 |
| Wo 95/06633 | 3/1995 | WIPO | C07C 327/32 |
| 9603427 | 2/1996 | WIPO . | |
| 9513832 | 5/1996 | WIPO . | |

*Primary Examiner*—John Kight
*Assistant Examiner*—Dameron Jones
*Attorney, Agent, or Firm*—Nikaido Marmelstein Murray & Oram, LLP

[57] ABSTRACT

Compounds useful for high resolution diagnostic imaging incorporate an imaging agent having a chelator that is linked by a metal-cleavable bond to a ligand that has affinity for a site removed from the site of diagnostic interest. Upon labelling, the ligand is cleaved leaving the labelled imaging agent free to localize at the site of diagnostic interest unhindered, while the ligand and any unlabelled imaging agent is sequestered to the removed site. By sequestering unlabelled imaging agent, the labelled imaging agent does not compete to occupy the site of interest, resulting in images of enhanced resolution.

19 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Thr  Lys  Pro  Pro  Arg
    1                          5

( 2 ) INFORMATION FOR SEQ ID NO:2:

```
( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Position 1 has either a
              dimethyl substituent or an N,N-dimethyl substituent."

( i x ) FEATURE:
        ( A ) NAME/KEY: Modified-site
        ( B ) LOCATION: 9
        ( D ) OTHER INFORMATION: /note= "Position 9 has an -OH
              substituent."

( x i ) SEQUENCE DESCRIPTION: SEQ ID NO:2:

Gly  Ser  Cys  Gly  Thr  Lys  Pro  Pro  Arg
 1                  5
```

SEQUESTERED IMAGING AGENTS

FIELD OF THE INVENTION

This invention relates to medical diagnostic imaging and specifically to compounds and their use in imaging in vivo sites of diagnostic interest.

BACKGROUND

The art of diagnostic imaging exploits agents that in binding or localizing site selectively within the body, help to resolve the image of diagnostic interest. Imaging agents generally consist of a targetting molecule that is labelled with a traceable element, the targetting molecule serving to carry the label to the site of diagnostic interest where it is detected by scanning tomography. Traceable elements commonly used in the art include radionuclide metals. However, an inherent problem with metal labels is that they do not bind well to many targetting molecules such as proteins, peptides and antibodies. Therefore, much of the label is not carried to the site of diagnostic interest. In order to overcome this problem, prior workers in the field have coupled chelating groups to targetting molecules that will readily form a stable coordination complex with the particular metal.

However, a persisting problem with metal labels is that labelling reactions yield an extreme excess of unlabelled agent versus labelled agent. For example, a typical labelling reaction involving the widely used radionuclide metal $^{99m}$Tc will yield one labelled agent for every thousand that are unlabelled. Unlabelled agents localize at the target site along with labelled agents and will compete with the labelled agent to occupy the site. Consequently, some of the labelled agent will be prevented from localizing at the site thereby adversely affecting the resolution of the image. Competitive binding is a particular problem when the targetting molecule is a protein, peptide or antibody having a finite number of binding sites at the diagnostic site. The problem of excess unlabelled agent is exacerbated by the fact that for diagnostic imaging purposes, and particularly scintigraphic imaging, only a very small quantity of traceable metal can be safely administered to an individual at any one time. Consequently only a small amount of labelled agent will localize at the target site.

In light of the inherent problems associated with imaging agents currently available, it would be desirable to provide a diagnostic imaging agent that localizes at a target site only when it is in a form labelled with a detectable metal and that is sequestered to a site removed from the diagnostic site when in unlabelled form.

SUMMARY OF THE INVENTION

According to one aspect of the invention, there is provided a compound useful for diagnostic imaging, comprising:
an imaging agent that localizes selectively at an in vivo site of diagnostic interest, the agent comprising a chelator for a traceable metal;
a ligand that localizes at an in vivo site removed from the site of diagnostic interest; and
a metal-cleavable bond coupling the chelator of the imaging agent to the ligand;
wherein said bond is cleaved upon formation of a coordination complex of the metal and chelator.

According to another aspect of the present invention, there is provided a method of imaging an in vivo site of diagnostic interest comprising the steps of introducing a traceable metal to a solution comprising a compound of the invention; administering the resulting solution to the patient; and then detecting localization of the traceable metal.

DETAILED DESCRIPTION OF THE INVENTION

Figure 1:
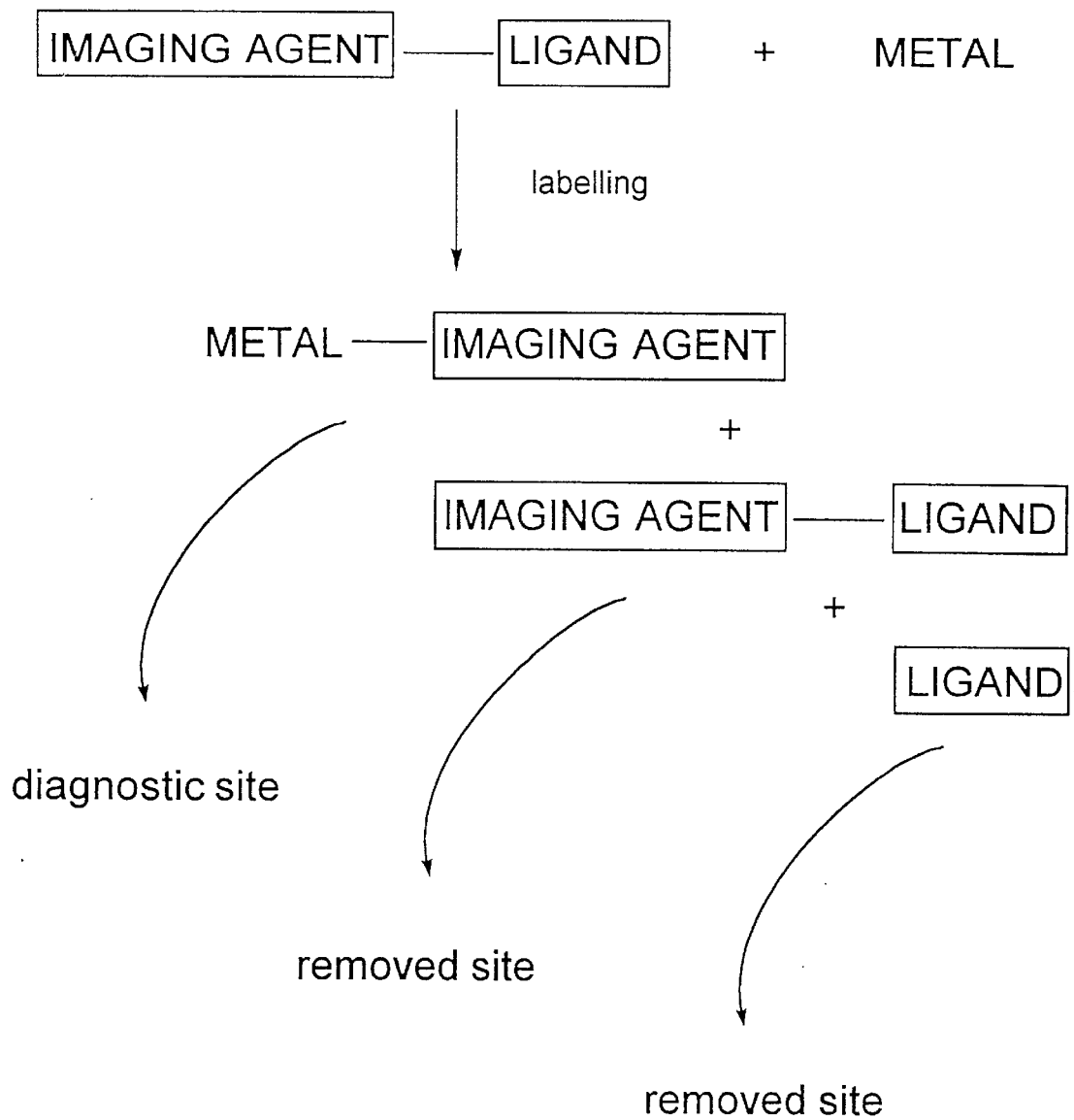
FIG. 1 is a schematic diagram illustrating the localization of products upon labelling compounds of the invention.

The present invention provides compounds useful for obtaining diagnostic images of high resolution. The compounds incorporate an imaging agent having a chelator that is linked by a metal-cleavable bond to a ligand that localizes at a site removed from the site of diagnostic interest. Upon labelling, the ligand is cleaved from the metal-imaging agent complex which is then free to localize at the site of diagnostic interest while the ligand is sequestered to the removed site. Unlabelled compound, the major product of typical labelling reactions, still incorporates the ligand and is also sequestered to the removed site. By sequestering unlabelled compound, the labelled imaging agent does not have to compete to occupy the diagnostic site. As a result, a greater percentage of labelled imaging agent accumulates at the diagnostic site than would otherwise, thereby facilitating images of greater resolution.

According to an aspect of the invention, there is provided a compound useful for diagnostic imaging, comprising:
an imaging agent that localizes selectively at an in vivo site of diagnostic interest, the agent comprising a chelator for a traceable metal;
a ligand that localizes at an in vivo site removed from the site of diagnostic interest; and
a metal-cleavable bond coupling the chelator of the imaging agent to the ligand;
wherein said bond is cleaved upon formation of a coordination complex of the metal and chelator.

The term "imaging agent" refers to a compound that is capable of localizing selectively at sites of diagnostic interest in vivo such as at a particular organ, tissue or cell type. An imaging agent useful in the invention also functions as a chelator that is capable of forming a complex with a traceable metal that is stable under physiological conditions. Many chelators that bind to radionuclide metals, and particularly those that bind $^{99m}$Tc, are tetradentate containing a combination of four nitrogen and sulfur metal-coordinating atoms ie. $N_4$, $N_3S$ and $N_2S_2$. However, chelators may incorporate other metal-coordinating atoms such as oxygen, phosphorous and selenium. For diagnostic imaging it is particularly desirable that the metal complex be highly stable in vivo so that the metal is not released from the chelator in substantial quantities free to accumulate in various non-target organs. Imaging agents according to the present invention can incorporate a wide variety of chelators, such as $N_3S$ chelators described in copending PCT application CA94/00395 filed on 18 Jul. 1994, and $N_2S_2$ chelators described in copending PCT application CA94/00479 filed on 31 Aug. 1994. Other suitable chelators are peptidic or peptide derivatives which incorporate a pendant sulfhydryl group for binding to $^{99m}$Tc. For example, suitable peptidic chelators are those described in copending U.S. application Ser. No. 08/279,155 filed on 22 Jul. 1994 which include a tripeptide having the formula DMG-a.a.-Cys wherein DMG is a derivatized amino acid residue N,N-dimethylglycine and a.a. is an amino acid residue that is most preferably Ser or Thr.

In some instances, the functions of metal chelation and site localization are both served by the chelator. Alternatively and typically imaging agents further incorporate a targetting molecule attached to the metal chelator either directly or through a linking group. The targetting molecule serves to carry the chelator and consequently a traceable metal to the site of diagnostic interest where it can be detected to produce an image. Targetting molecules include, but are not limited to, steroids, antibodies, proteins, peptides, nucleotides and saccharides. Suitable targetting molecules include proteins and peptides, particularly those capable of binding with specificity to cell surface receptors characteristic of a particular pathology. Preferably, targetting molecules are peptides or derivatives thereof comprising 3 or more amino acid residues i.e. 3 to 50 residues and more preferably 3 to 10 residues. In an embodiment of the invention, targetting molecules are peptides that bind to cell surface receptors such as those described in copending U.S. Ser. No. 08/171,737 (Pollak et al) which incorporate the amino acid sequence TKPPR(SEQ ID NO: 1).

To form the imaging agent, targetting molecules are preferably attached to the chelator by a linking group that is selected so that the targetting molecule retains its localizing function and the chelator retains its metal binding function. Suitable linking groups include alkyl chains and amino acid chains functionalized with reactive groups for coupling to the targetting molecule and chelator. When either the chelator or targetting molecule is peptidic, the linking group is preferably an amino acid chain, for example amino acid chains of 1–5 residues and preferably 1–3 residues.

When the chelator itself has suitable localizing properties, attachment of a targetting molecule may be unnecessary. For example, the chelator mercapto-acetyl-glycyl-glycyl-glycine (MAG3) described in U.S. Pat. No. 4,980,147 (Fritzberg et al), binds and carries $^{99m}$Tc to renal tissues for imaging. Other chelators having localizing properties include 4-quinolone antibiotic compounds described in WO 93/03,772 (Solanki) which are useful for imaging focal inflammation and carbohydrates such as glucarate described in U.S. Pat. No. 4,946,668 (Daddona et al) which are useful for imaging calcified tissue.

A "ligand" according to the present invention refers to a group that localizes at an in vivo site other than the diagnostic site i.e. has less affinity for the diagnostic site. The suitability of a ligand for coupling to a given imaging agent may be determined by comparing the in vivo biodistribution of the imaging agent and the ligand when both are labelled independently of the other. The ligand will localize at the diagnostic site to a lesser extent than the imaging agent and most desirably not at all.

It will be appreciated that ligands may also be compounds that retard the rate at which the attached but unlabelled imaging agent would otherwise localize at the site of diagnostic interest. In this instance, the labelled imaging agent would occupy the diagnostic site first, forcing the unlabelled compound to localize elsewhere. Also, ligands can be selected that localize at more than one specific removed site, for example diffuse sites such as the vascular endothelium or blood cells, provided that these sites are other than the diagnostic site. Ideally, the ligand is selected to target a removed site that is encountered soon after administration, i.e. into the blood stream, and is most preferably encountered before the diagnostic site. Suitably the ligand is selected to target such removed sites as the liver, kidney, lungs, vascular endothelium or blood cells.

Ligands include, but are not limited to steroids, antibodies, proteins, peptides, nucleotides and saccharides. Suitable ligands include galactosyl residues which localize in hepatic tissue; vasoactive intestinal peptide (VIP) which localizes in the lungs; and glycosaminoglycans (GAG) which localizes in kidneys. Other suitable ligands include compounds that bind to epidermal growth factor (EGF) receptors, which are highly expressed in hepatic tissue, including the EGF protein and fragments thereof. In general, compounds that are highly hydrophobic or lipophilic are suitable ligands since they tend to accumulate in the lungs or in blood cells.

In the compounds of the invention, a ligand is coupled to the imaging agent through a covalent bond to a metal coordinating atom of the chelator that is cleaved upon formation of a coordination complex of the metal and chelator. By coupling through a metal-cleavable bond, the ligand serves to prevent unlabelled imaging agent from accumulating at the diagnostic site, thereby allowing labelled imaging agent to accumulate at the site of diagnostic interest without competition from its unlabelled counterpart. The ligand is coupled by a functional group attached to the ligand forming a covalent bond to a coordinating atom of the chelator which is cleavable upon formation of a coordination complex between the chelator and the metal. A functional group is selected according to the type of coordinating atom of the chelator to which it is bound. When the coordinating atom is sulfur, suitable functional groups are metal-cleavable thiol protecting groups. Several examples of thiol protecting groups that are cleaved by traceable metals are described in *Protective Groups in Organic Synthesis,* 2nd ed., Greene and Wuts, John Wiley & Sons, New York, 1991. For example, ligands may be functionalized by techniques established in the art of organic chemistry with various para-substituted benzyl groups such as p-methoxybenzyl, p-nitrobenzyl; triphenylmethyl; t-butyl; adamantyl; dihydropyran; and maleimide. A ligand incorporating a free amino substituent can be functionalized with a thiol-protecting group such as a dihydropyran group, by reacting the ligand with dihydropyran carboxylic acid to form an amide linkage. A chelator may then be coupled to the dihydropyran functionalized ligand by reacting the chelator and the ligand in the presence of dimethylformamide (DMF).

When the coordinating atom is an amino nitrogen, suitable functional groups include metal-cleavable amino protecting groups, for example, ethyl esters such as trichloroethyl ester, trimethylsilylethyl ester and phenyl-ethyl ester; as well as vinyl ester; and allyl ester groups. Amino protecting groups bind to the nitrogen coordinating atom of a chelator to form carbamate linkages that are metal-cleavable. In the case where the coordinating atom is an amide nitrogen, suitable functional groups include metal-cleavable amide protecting groups such as an allyl group. A chelator containing an oxygen coordinating atom may be coupled to a functional group that is a metal-cleavable hydroxy protecting group such as methylthiomethyl and t-butylthiomethyl. Conditions and reagents for coupling and cleaving metal-cleavable protecting groups to ligands are described in Greene and Wuts (supra).

In a particular embodiment of the invention, the ligand is a galactosyl residue that is functionalized with a maleimido group for coupling to the chelator of an imaging agent. The ligand may be prepared from a commercially available bromo-galactosyl residue such as 2,3,4, 6-tetra-O-acetyl-α-

D-galactopyranosyl bromide (Sigma) which is reacted with an amino-protected alkanol such as N-(t-butoxycarbonyl)-3-amino-1-propanol to give an aminoalkyl galactosyl residue upon amino-deprotection. The maleimide is then attached to the free amino group by reacting it with sodium sulfo-SMCC (Pierce).

In a specific embodiment of the invention, the compound incorporates an imaging agent comprising the chelator DMG-Ser-Cys, the targetting moiety TKPPR(SEQ ID NO: 1) and a galactosyl residue that serves as a ligand, the compound corresponding to the formula (I):

solution in oxo, dioxo or nitrido form, for example pertechnetate ($^{99m}TcO_4^-$) or perrhenate, with a suitable reducing agent such as stannous chloride. Alternatively, radiolabelled imaging agents may be formed by a transchelation reaction which entails the use of the metal in the form of a weak metal complex such as technetium-gluconate, heptagluconate, tartrate or citrate to give the desired labelled imaging agent. Transchelation reactions are typically heated to facilitate conversion of technetium from the weak complex to a stable complex with the chelator, for example in a boiling hot water bath.

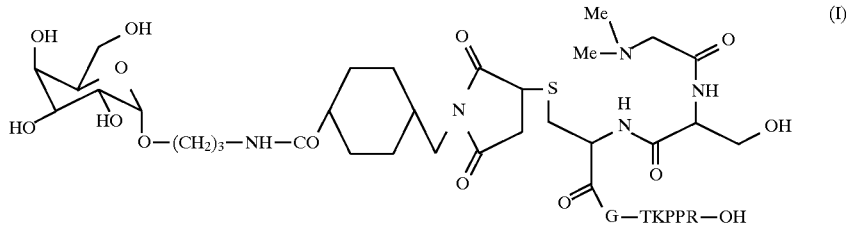

Ligands and/or imaging agents that are peptidic are commercially available or may be synthesized de novo by solid phase techniques or by recombinant DNA techniques. Solid-phase peptide synthesis generally involves the use of automated synthesizers and an appropriate support as the solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of the peptide from the support, and the peptide is then isolated. Common purification techniques include reversed-phase HPLC using acetonitrile as solvent and trifluoroacetic acid as an ion-pairing agent. Solid phase peptide synthesis is an established technique described in detail in Stewart and Young, *Solid Phase Peptide Synthesis,* 2nd Edition, 1984, Pierce Chemical Company, Rockford, Ill. Alternatively, peptides may be synthesized in solution or on a solid phase in small blocks and subsequently ligated to give the desired sequence.

The term "traceable metal" refers to any metal atom that is in a state capable of forming stable coordination complex with a chelator of an imaging agent and can be detected in vivo. Traceable metals that are capable of forming complexes include the transition metals, lanthanide metals and actinide metals. For use in MRI, the metal is a paramagnetic metal atom such as divalent and trivalent chromium, manganese, iron, cobalt, nickel, copper, praseodymium, neodymium, samarium, ytterbium, terbium, dysprosium, holmium, erbium and gadolinium. The more preferred metals for MRI are those exhibiting a strong magnetic moment, such as gadolinium and manganese. The halide salt, in particular chloride salt, or oxide of these metals are capable of forming coordination complexes with a desired ligand and are suitable for the present invention. Radionuclide labelled imaging agents employ metal isotopes that include β-emitters such as rhenium-186 and -188; and γ-emitters such as technetium-99m. The metal most preferred for radiodiagnostic imaging is technetium-99m due to its advantageous half life of 6 hours and inexpensive preparation from a molybdenum-99 generator. Technetium and rhenium labelling is accomplished by procedures established in the art. Either metal may be introduced to a chelator in aqueous In another aspect of the invention, there is provided a method of imaging an in vivo site of diagnostic interest comprising the steps of introducing a traceable metal to a solution comprising a compound according to the invention to form a labelled solution; administering the labelled solution in vivo; and detecting localization of the traceable metal. The compound may be administered to a mammal intralymphatically, intraperitoneally, and preferably intravenously in a pharmaceutically acceptable solution such as saline or blood plasma medium. The amount administered is dependent upon the toxicity profile of the chosen imaging agent and ligand as well as that of the metal. When the metal is a radionuclide, a solution having an activity of about 0.01 to 100 mCi is administered to a 70 kg individual and preferably 10 to 50 mCi. Localization of the radionuclide metal in vivo is tracked by standard scintigraphic techniques at an appropriate time subsequent to its administration or by standard MRI techniques for paramagnetic metals. The time at which an image may be obtained will depend upon the pharmacokinetic profile of the imaging agent, for example most peptide imaging agent will localize rapidly allowing for an image to be obtained within 3 hours and often within 1 hour while antibody imaging agents typically take longer.

EXAMPLE 1

Synthesis of conjugate 4 [peptide DMG-Ser-Cys-G-TKPPR-OH [SEQ ID NO: 2] protected at the Cys thiol with 3'-(4"-N-maleidomethylcyclohexyl-1"-carboxy)-aminopropyl-α-D-galactopyranoside 3]

Figure 2:
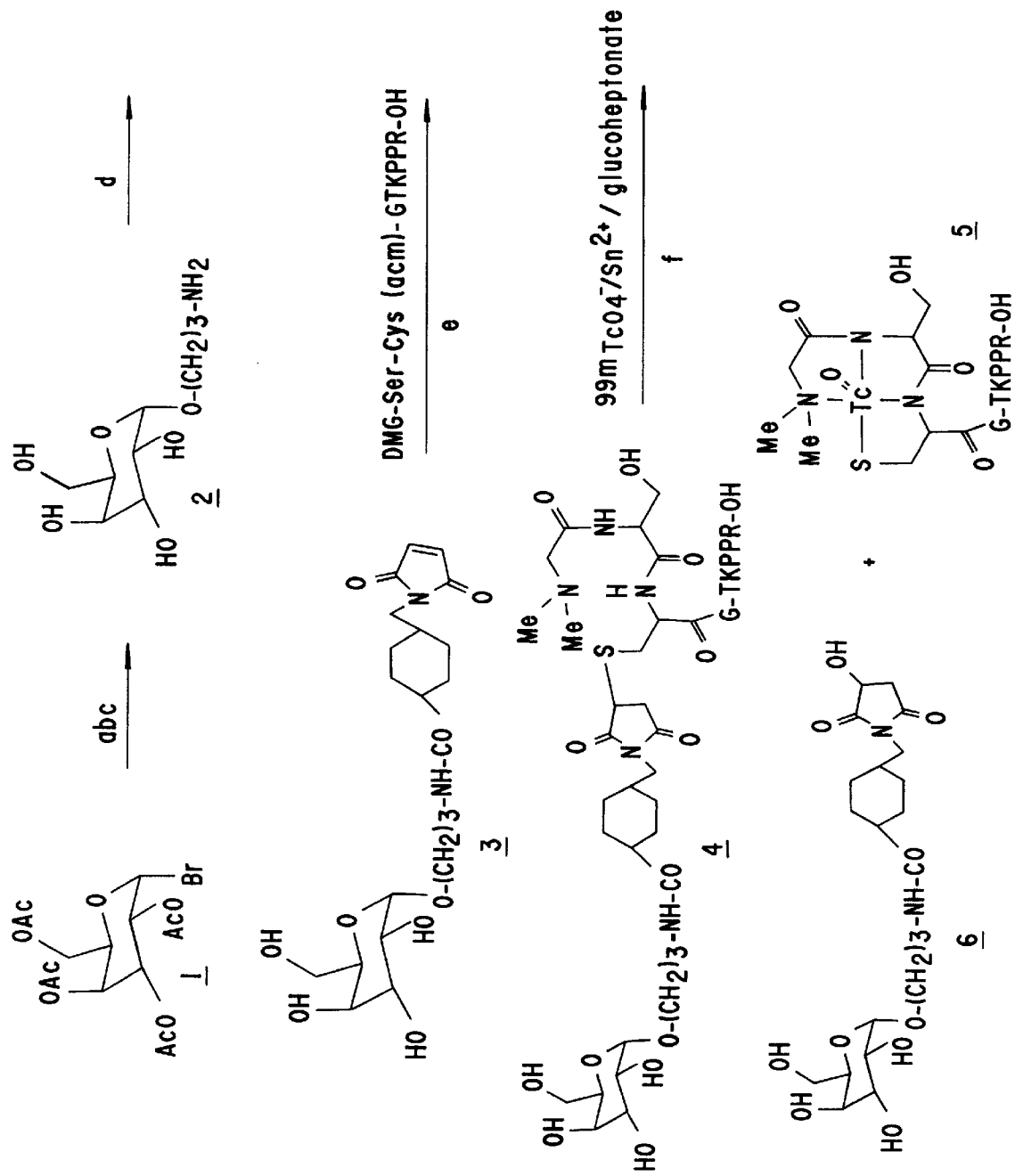
FIG. 2 is a schematic diagram illustrating the synthesis and labelling of a compound according to a specific embodiment of the invention.

Conjugate 4 is synthesized according to the steps illustrated in FIG. 2 and described in detail as follows:

a. 2,3,4,6-tetra-O-acetyl-(3'-t-butoxycarbonylaminopropyl)-α-D-galactopyranoside 2,3,4, 6-tetra-O-acetyl-α-D-galactopyranosyl bromide 1 (4.10 g, 10.0 mMol) is reacted with N-(t-butoxycarbonyl)-3-amino-1-propanol (1.75 g, 10.0 mmol), anhydrous zinc chloride (1.36 g, 10.0 mMol), 18-crown-6 (2.64 g, 10.0 mmol) and potassium chloride (0.74 g, 10.0 mmol) in dichloromethane (50 mL) at room temperature for 36 hours. After work up, the product, 2,3,4,6-tetra-O-acetyl-(3'-t-butoxycarbonylaminoproply)-α-D-galactopyranoside is isolated in approximately 60% yield (3 g). $C_{22}H_{35}NO_{12}$ MW 505.53 b. (3'-t-butoxycarbonylaminoproply)-α-D-galactopyranoside 2,3,4,6-tetra-O-acetyl-(3'-t-butoxycarbonylaminopropyl)-α-D-galactopyranoside (2.52 g, 5.0 mMol) is dissolved in anhydrous methanol (50 mL) and a solution of sodium methoxide in methanol (0.5M, 1.0 mMol) is added. The reaction mixture is allowed to react at room temperature for 3 hours. After standard workup, the product (3'-t-butoxycarbonylaminoproply)-α-D-galactopyranoside is isolated in approximately 80% yield (1.35 g). $C_{13}H27NO_8$ MW 337.37 c. 3'-aminopropyl-α-D-galactopyranoside 2

(3'-t-butoxycarbonylaminopropyl)-α-D-galactopyranoside (1.13 g, 3.4 mMol) is deprotected in a mixture (10 mL) containing 95% of trifluoroacetic acid (TFA) and 5% of water at room temperature for 3 hours. After evaporation of TFA in vacuum, the product 2 is obtained as a TFA salt in approximately 95% yield (1.1 g). $C_9H_{20}NO_6 \cdot CF_3COOH$ MW 352.30 d. 3'-(4"-N-maleidomethylcyclohexyl-1"-carboxy)-aminopropyl-α-D-galactopyranoside 3

3'-aminopropyl-α-D-galactopyranoside 2 TFA salt (0.35 g, 1 mmol) is dissolved in distilled water (3.0 mL) and sodium carbonate (0.21 g, 2.0 mmol) is added. The pH of this solution is adjusted to 7.5 by adding additional sodium carbonate. A solution of sodium sulfo-SMCC (0.48 g, 1.1 mmol in 2 mL of distilled water) is added and the reaction mixture is stirred at room temperature for 3 hours. During this period, pH of the solution is adjusted to pH=7.5 with sodium carbonate. After 3 hours, pH of the solution is adjusted to 7.0 by adding small aliquot of 1.0M monosodium phosphate solution to yield the product 3. $C_{21}H_{33}N_2O_7$ MW 425.50 e. conjugate 4

A 1.0 mL volume of the reaction mixture containing about 0.2 mmol of the 3'-(4"-N-maleidomethylcyclohexyl-1"-carboxy)-aminopropyl-α-D-galactopyranoside 3 is added to a solution of the peptidic imaging agent DMG-Ser-Cys(acm)-G-TKPPR-OH [SEQ ID NO: 2] (100 mg, 0.1 mmol, in 2.0 mL of distilled water). The pH of this reaction solution is measured, and, if necessary, adjusted to pH=7.0. The reaction is monitored by analytical HPLC (C18 column, acetonitrile/0.1% TFA/water gradient). After 1 hour, the deprotected peptide is completely reacted and the reaction mixture is lyophilized. This material is purified on preparative HPLC (C18 reverse phase column, acetonitrile/0.1% TFA water/0.1% TFA gradient), and approximately 40 mg (35%) of the conjugate 4 [peptide DMG-Ser-Cys-G-TKPPR-OH [SEQ ID NO: 209 protected at the Cys thiol with 3'-(4"-N-maleidomethylcyclohexyl-1"-carboxy)-aminopropyl-α-D-galactopyranoside] is obtained. $C_{59}H_{100}N_{15}O_{19}S$ MW 1355.60

EXAMPLE 2 f. Labelling of conjugate 4 with $^{99m}Tc$ Pertechnetate

Solutions A and B were prepared as follows:

Solution A: To a solution of conjugate 4 from example 1 (200 μg) in saline (200 μL) in a 3 mL vacutainer with septum is injected a solution of sodium Tc-99m pertechnetate (10 mCi/100 μL).

Solution B: To an empty 3 mL vacutainer with septum is added 1 mL of sodium gluconate solution (10 mg/mL). 20 μL of stannous chloride solution (20 mg/mL in 1N HCl) is injected directly into the gluconate, and the solution is shaken gently to mix.

To solution A is injected 100 μL of solution B. followed by a brief gently swirling to mix. The vacutainer is vented to air with a 26 gauge needle through the septum, and heated in a boiling water bath for 10 minutes followed by cooling to room temperature. The resulting solution of $^{99m}Tc$ labelled imaging agent 5 and the thiol protecting group (sequestering group) 3'-(4"-N-(3-hydroxysuccinimidomethyl)cyclohexyl-1"-carboxy)-aminopropyl-α-D-galactopyranoside 6 is analyzed by HPLC (C18 reverse phase column, acetonitrile/0.1% TFA and water/0.1% TFA gradient), for radiochemical purity and yield (>90%).

---

We claim:

1. A compound useful for diagnostic imaging at a site of diagnostic interest, comprising an imaging agent-ligand complex comprising:
   an imaging agent comprising a chelator for a traceable metal;
   a ligand capable of localizing in vivo at a site removed from the site of diagnostic interest; and
   a metal-cleavable bond coupling the chelator of the imaging agent to the ligand, wherein the metal-cleavable bond is cleavable in vivo or in vitro to form a metal-imaging agent complex and a cleaved ligand;
   wherein the metal-imaging agent complex localizes selectively in vivo at the site of diagnostic interest and the cleaved ligand and any uncleaved imaging agent-ligand complex present localize in vivo at the site removed from the site of diagnostic interest.

2. A compound according to claim 1, wherein the imaging agent comprises a targetting molecule attached to the chelator.

3. A compound according to claim 1, wherein said metal-cleavable bond is between the ligand and a coordinating atom of the chelator.

4. A compound according to claim 3, wherein said metal-cleavable bond is between a coordinating atom of the chelator and a functional group of the ligand.

5. A compound according to claim 4, wherein the coordinating atom of the chelator is sulfur.

6. A compound according to claim 5, wherein the functional group of the ligand is a sulfur protecting group attached to the ligand.

7. A compound according to claim 6, wherein the sulfur protecting group is maleimide.

8. A compound according to claim 1, wherein the ligand is a galactosyl residue.

9. A compound according to claim 7, wherein the ligand is a galactosyl residue.

10. A compound according to claim 1, wherein the chelator is N,N-dimethyl-Gly-Ser-Cys.

11. A compound according to claim 7, wherein the chelator is N,N-dimethyl-Gly-Ser-Cys.

12. A compound according to claim 2, wherein the targetting molecule is a peptide comprising the sequence TKPPR [SEQ ID NO: 1].

13. A compound according to claim 2, wherein the imaging agent is N,N-dimethyl-Gly-Ser-Cys-Gly-Thr-Lys-Pro-Pro-Arg-OH [SEQ ID NO: 2].

14. A compound of the formula (I)

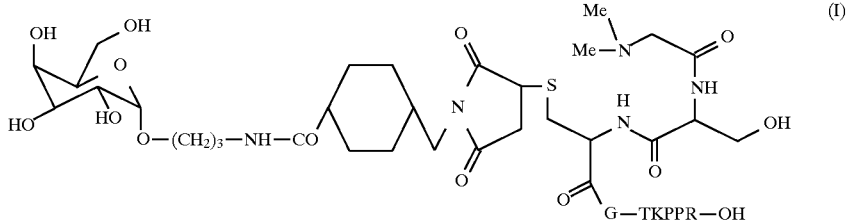

15. A compound according to claim 1, wherein the traceable metal is $^{99m}$Tc.

16. A compound according to claim 14, wherein the traceable metal is $^{99m}$Tc.

17. A method of imaging an in vivo site of diagnostic interest comprising the steps of introducing a traceable tl to a solution comprising a compound according to claim 1 to form a labelled solution; administering the labelled solution in vivo; and detecting localization of the traceable metal.

18. A method according to claim 17, wherein the traceable metal is $^{99m}$Tc.

19. A method of imaging an in vivo site of diagnostic interest comprising the steps of introducing a traceable metal to a solution comprising a compound according to claim 14 to form a labelled solution; administering the labelled solution in vivo; and detecting localization of the traceable metal.

* * * * *